United States Patent [19]
Sekiguchi

[11] Patent Number: 5,574,473
[45] Date of Patent: Nov. 12, 1996

[54] IMAGE DISPLAY APPARATUS

[75] Inventor: Nobutoshi Sekiguchi, Hidaka, Japan

[73] Assignee: Olympus Optical Co., Ltd., Tokyo, Japan

[21] Appl. No.: 285,200

[22] Filed: Aug. 3, 1994

[30] Foreign Application Priority Data

Aug. 26, 1993 [JP] Japan .................................. 5-211557

[51] Int. Cl.⁶ .................................................. G09G 5/00
[52] U.S. Cl. .............................. 345/8; 345/32; 359/370; 359/577
[58] Field of Search .......................... 345/8, 32; 351/209, 351/210, 216; 359/577, 370, 559

[56] References Cited

U.S. PATENT DOCUMENTS

| | | | |
|---|---|---|---|
| 3,583,794 | 6/1971 | Newman | 351/210 |
| 4,028,725 | 6/1977 | Lewis . | |
| 4,048,653 | 9/1977 | Spooner | 345/8 |
| 4,347,508 | 3/1982 | Spooner . | |
| 4,735,498 | 4/1988 | Uddén et al. | 351/210 |
| 4,743,200 | 3/1988 | Welch et al. | 345/8 |
| 4,772,101 | 9/1988 | Liu . | |
| 4,880,286 | 11/1989 | Ih . | |
| 4,897,715 | 1/1990 | Beamon, III | 345/8 |
| 4,984,179 | 1/1991 | Waldern | 345/8 |
| 5,079,555 | 1/1992 | Turpin . | |
| 5,106,179 | 4/1992 | Kamaya . | |
| 5,345,281 | 9/1994 | Taboada et al. | 351/210 |
| 5,382,989 | 1/1995 | Uomori et al. | 351/210 |
| 5,426,521 | 6/1995 | Chen et al. | 359/559 |

FOREIGN PATENT DOCUMENTS

| | | |
|---|---|---|
| 0473343A1 | 3/1992 | European Pat. Off. . |
| 59-119982 | 7/1984 | Japan . |
| 1-124434 | 5/1989 | Japan . |
| 2-136818 | 5/1990 | Japan . |
| 3-51167 | 8/1991 | Japan . |
| 3-21487 | 9/1991 | Japan . |
| WO84/00831 | 3/1984 | WIPO . |

OTHER PUBLICATIONS

Patent Abstracts of Japan, vol. 15, No. 309 (P–1235) Aug. 7, 1991 & JP–A–03 110 592 (Casio) May 10, 1991.
Patent Abstracts of Japan, vol. 14, No. 369 (P–1090) Aug. 9, 1990 & JP–A–02 136 818 (Sony) May 25, 1990.
SPIE Display System Optics, vol. 778, 1987, pp. 70–78, M. Shenker, "Optical Design Criteria for Binocular Helmet-Mounted Displays".

*Primary Examiner*—Richard Hjerpe
*Assistant Examiner*—Juliana S. Kim
*Attorney, Agent, or Firm*—Frishauf, Holtz, Goodman, Langer & Chick

[57] ABSTRACT

An image display apparatus comprises an image display unit capable of generating and displaying a plurality of coherent point light source pairs, a light transmission unit for focusing the point light source pairs on the pupil plane of an observer's eye so that an image is formed on the retina of the eye by the effect of optical interference, a visual axis detector for monitoring the movements of the eye and detecting the visual axis direction thereof, and an image display correcting unit for restricting a distortion of the image, caused by the eye movements, within its tolerance in accordance with data detected by the visual axis detector. The image display correcting unit includes an optical member set in an optical path between the image display unit and a lens, and an optical member drive unit for tilting the optical member for a given angle in a predetermined direction.

12 Claims, 4 Drawing Sheets

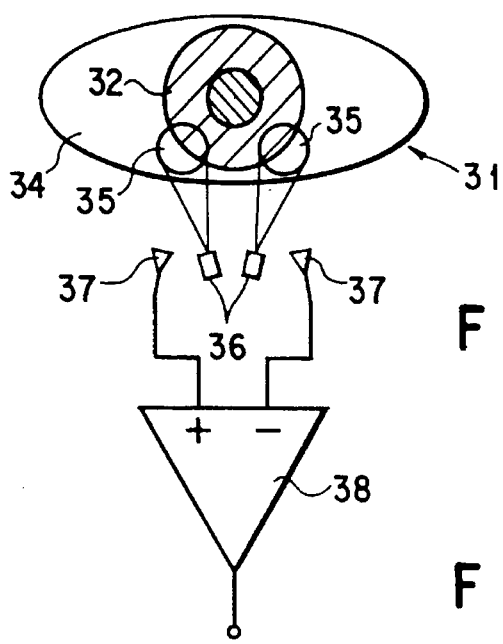
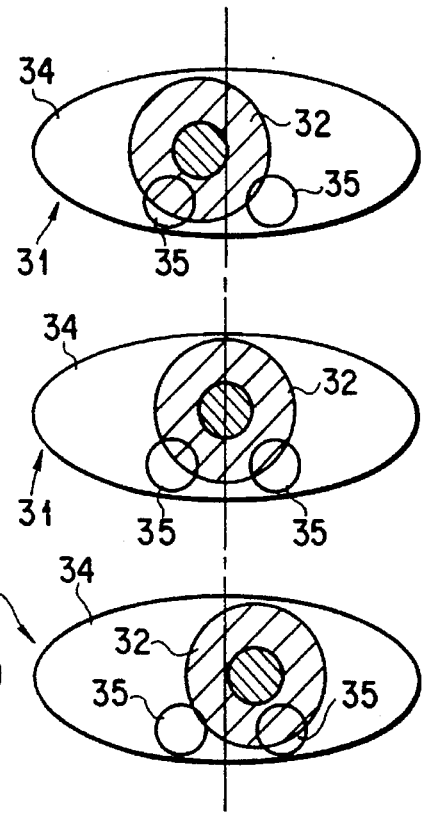
FIG. 3A
FIG. 3B
FIG. 3C
FIG. 3D
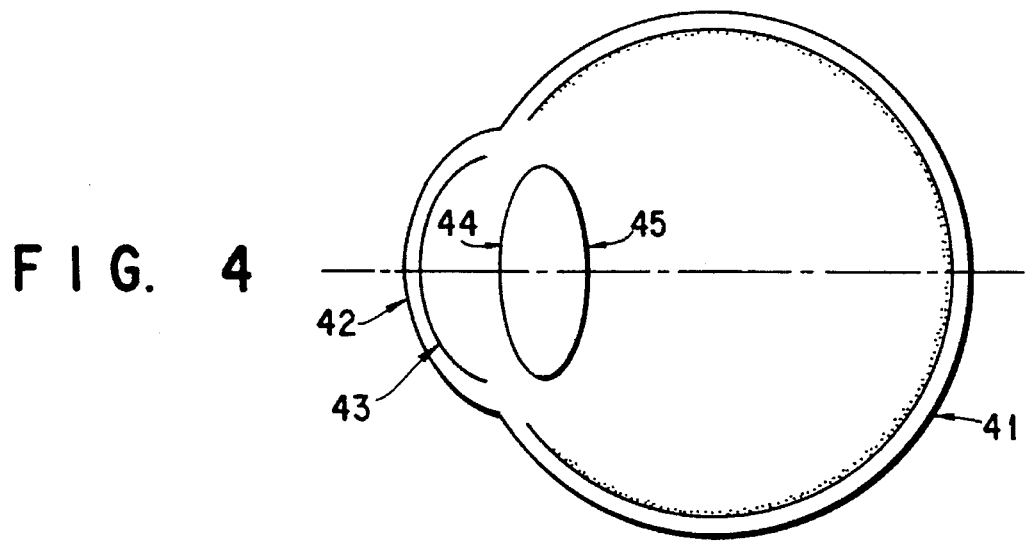
FIG. 4

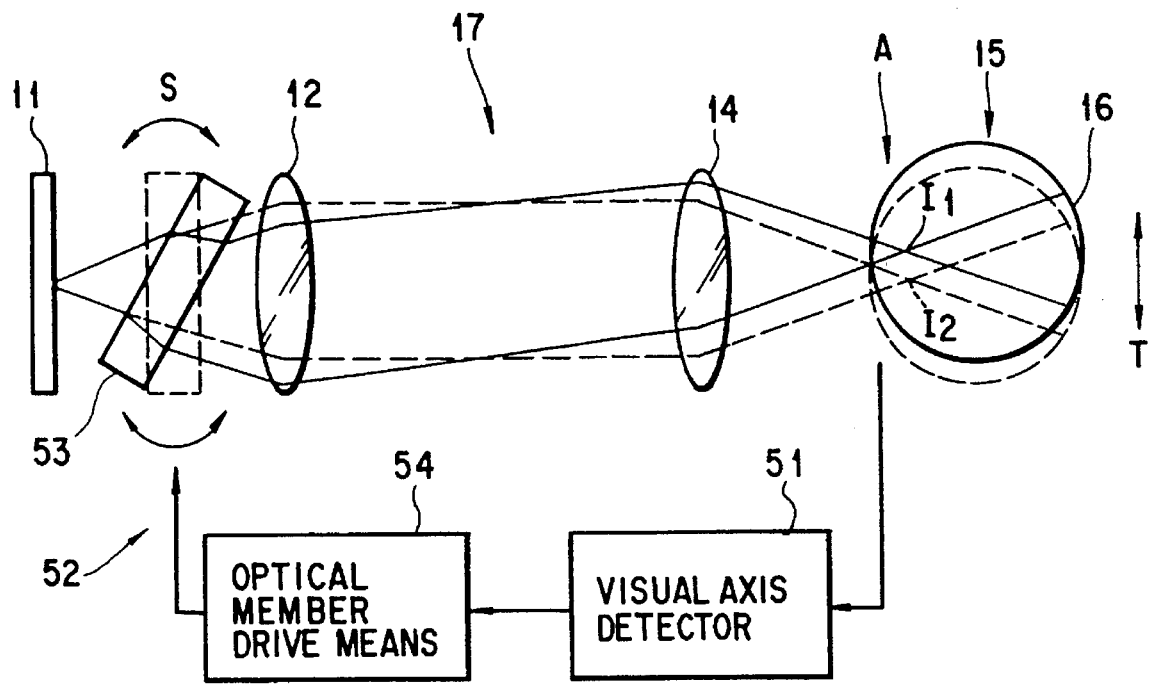
F I G. 5
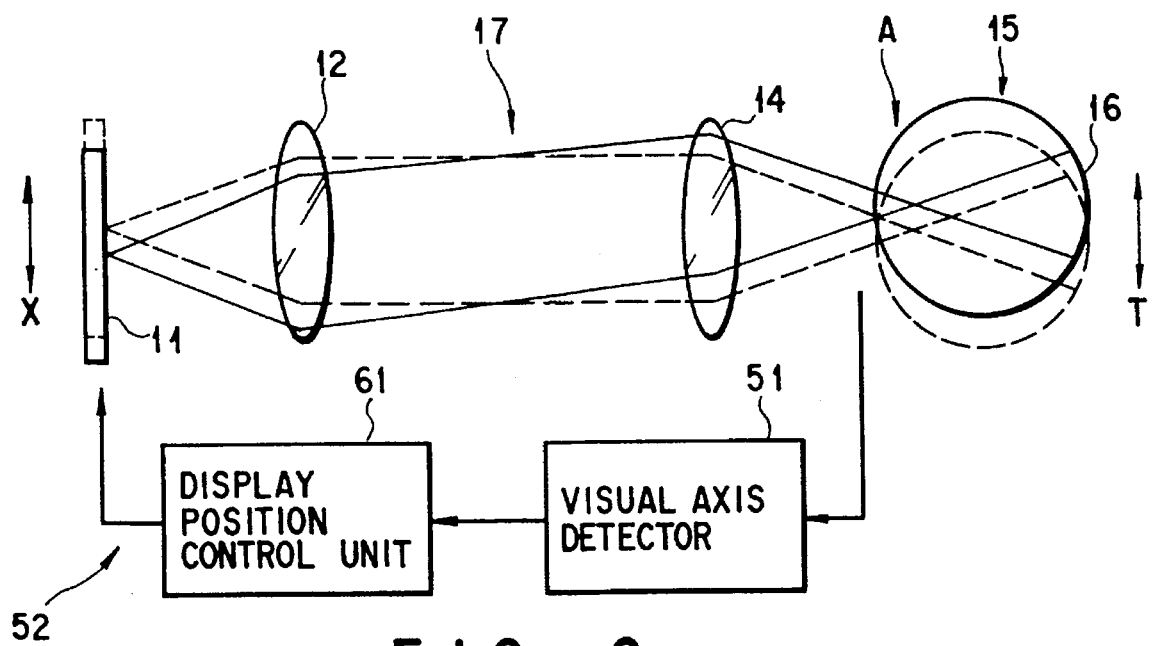
F I G. 6

IMAGE DISPLAY APPARATUS

BACKGROUND OF THE INVENTION

1. Field of the Invention

The present invention relates to an image display apparatus for projecting and displaying a wide-field-angle, high-definition image on the retina of an eye.

2. Description of the Related Art

In a conventional image display apparatus (not shown), an image display unit and the retina of an observer's eye are conjugate with each other. Accordingly, an image generated by the display unit is transmitted through an image transmission medium, and then formed on the retina by means of the optical system of the eye.

In the image display unit of this type, it is difficult to attain both wide-field-angle and high-definition simultaneously. If the image generated and displayed by the image display unit is enlarged in order to obtain a wide-field-angle, the spatial resolution would be lowered and corresponding image quality would be degraded remarkably. For example, each pixel of the image display unit may be enlarged to be visible or the spacial frequency of the image formed on the retina may be limited.

In the conventional image display apparatus, moreover, the quality of a retinal image depends on the refractive power of the observer's eye. Therefore, the refractive power of the ametropic eye must be corrected, in many ways, such as with spectacles, contact lenses, visibility adjustment equipment, or the like.

Proposed in Jpn. Pat. Appln. No. 4-302160 (U.S. Pat. No. 08/150,358), which the assignee of the present application filed, is an apparatus which projects and displays a wide-field-angle, high-definition image on the retina without being limited by the resolution of the image display unit or the optical properties of the eye.

This apparatus has the following principle of operation. A plurality of coherent point light source pairs generated and displayed by the image display unit are focused on the pupil plane of the eye with optical means, whereby a number of interference fringes are formed on the retina. These interference fringes are synthesized to form a retinal image.

According to this principle, the image display unit and the retina are not conjugate with each other, so that the spatial resolution characteristics of the optical system are not limited by those of the display unit itself. Thus, the image can be displayed in a high contrast even at high spatial frequencies.

The field-angle can be determined independently of the spatial resolution characteristics and is simply based on the F-number of an eyepiece or the size of the pixels of the image display. Thus, a wide-field-angle, high-definition image can be projected and displayed on the retina.

Utilizing the effect of optical interference, however, the above-described apparatus is subject to the following drawback. When the observers eye moves, the the phase of the interference fringes which constitute the image is changed. Since the rate of this phase change with eye movements depends on the fringe spatial frequency, the resulting retinal image is seriously degraded. If the direction of the observer's visual axis is inevitably changed, therefore, the resulting retinal image is distorted.

SUMMARY OF THE INVENTION

The present invention has been contrived in order to eliminate the aforesaid drawback, and its object is to provide an image display apparatus capable of projecting and displaying a wide-field-angle, high-definition image on the retina by restraining a distortion of a retinal image caused by an observer's eye movements.

In order to achieve the above object, an image display apparatus according to the present invention comprises: display means for generating and displaying a plurality of coherent point light source pairs; optical means for focusing images of the point light source pairs, generated and displayed by the display means, on the pupil plane of an observer's eye so that an image is formed on the retina by the effect of optical interference; visual axis detecting means for monitoring the movements of the eye and detecting the direction of visual axis thereof; and an optical correcting unit for reducing a distortion of the image caused by the eye movements into the tolerance range thereof, in accordance with data detected by the visual axis detecting means.

According to this arrangement, the images of the point light source pairs generated and displayed by the display means are focused on the pupil plane of the eye by the optical means in a manner such that the distortion of the image is reduced into the tolerance range by the optical correcting unit.

Thus, according to the image display apparatus of the present invention, the images of the point light source pairs generated and displayed by the display means are focused on the pupil plane after the distortion of the image caused by the observer's eye movements is reduced by means of the optical correcting unit. As a result, a wide-field-angle, high-definition image can be projected and displayed on the retina.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2A is a view showing the optical axes of the eye and an image display unit are aligned;

FIG. 2B is a view showing a state in which the optical axis of the eye is shifted downward;

FIG. 3A is a view showing an arrangement with which the direction of visual axis is measured;

FIGS. 3B, 3C and 3D are views for illustrating the relationships between the state of eye movements and spot positions;

FIG. 4 is a view showing another example in which light reflection at corneal surface and at optical interfaces in the eye are utilized in detecting the visual axis;

FIG. 5 is a schematic view showing an arrangement of an image display apparatus according to a first embodiment of the present invention;

FIG. 6 is a schematic view showing an arrangement of an image display apparatus according to a second embodiment of the invention;

DETAILED DESCRIPTION OF THE PREFERRED EMBODIMENTS

The following is a description of the principle of retinal image formation to which the interference method is applied, followed by a description of the principle of the present invention and various embodiments of the invention based on this principle.

Figure 1:
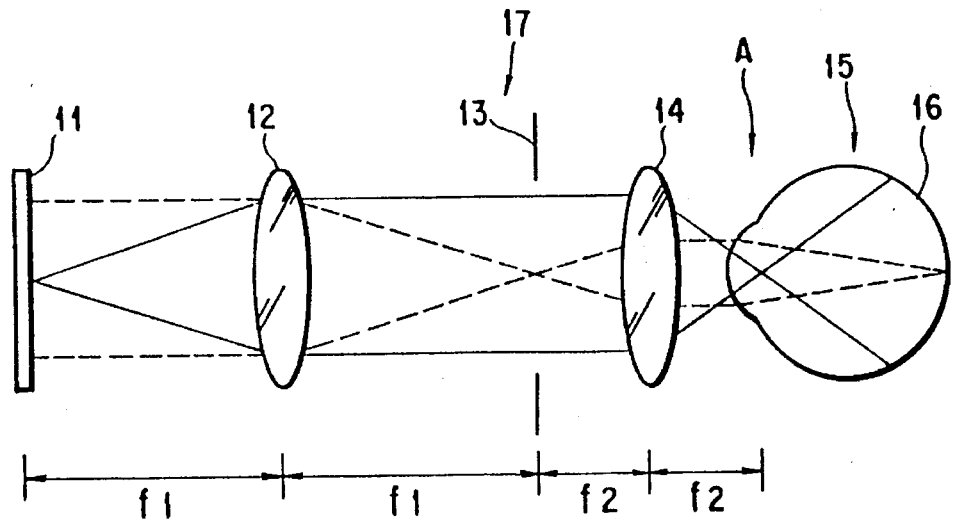
FIG. 1 is a schematic view showing an arrangement of an image display optical system, illustrating the principle of retinal image formation with interference method.

FIG. 1 schematically shows an arrangement of an image display optical system for illustrating the principle of retinal image formation to which the interference method is applied.

As shown in FIG. 1, the image display optical system to which the present principle is applied comprises an image display unit 11 capable of generating and displaying a plurality of coherent point light source pairs (not an image itself intended to be displayed to the observer) and a light transmission unit 17 for focusing the point light source pairs, generated and displayed by the display unit 11, on the pupil plane A of an observer's eye 15 so that an image is formed on the retina 16 of the eye 15 by the effect of optical interference.

The light transmission unit 17 includes a lens 12 (focal length: $f_1$) and an eyepiece 14 (focal length: $f_2$), which are arranged so that the image-side focal plane of the lens 12 is coincident with the object-side focal plane of the eyepiece 14. A mask 13 is located in the object-side focal plane of the eyepiece 14 or the image-side focal plane of the lens 12, thereby defining the range and shape of the field of view.

Moreover, the image display unit 11 is located in the object-side focal plane of the lens 12, while the pupil plane A of the observer's eye 15 is aligned to the image-side focal plane of the eyepiece 14.

According to this arrangement, the relationships between the image display unit 11 and the pupil plane A of the eye 15 and between the image-side focal plane of the lens 12 and the retina 16 are adjusted to be optically conjugate with each other.

The coherent point light source pairs, generated and displayed by the image display unit 11, are focused on the pupil plane A of the eye 15 and Young's interference fringes are then formed on the retina 16 of the eye 15.

In general, images are expressed as the sum of sinusoidal waves of various spatial frequencies, orientations, amplitudes, and phases. Therefore, if a plurality of Young's interference fringes are formed on the retina 16 by focusing the respective images of the point light source pairs on the pupil plane A of the eye 15, a retinal image is formed by synthesizing these interference fringes.

If only the paired point light sources are coherent, that is, if the unpaired ones are incoherent each other, in particular, images formed on the image display unit 11 are Fourier-transformed at the imageside focal plane of the lens 12 or at the object-side focal plane of the eyepiece 14. Thus when a Fourier-transformed image is generated and displayed by means of the image display unit 11, an image equivalent to the original image is formed on the image-side focal plane of the lens 12.

The original image is transmitted to the retina 16 which is optically conjugate with the image-side focal plane of the lens 12, and is formed as the retinal image. Thus, the Fourier-transformed image generated and displayed by the image display unit 11, that is, original image, is formed on the retina 16.

This principle has the following advantages over that of a conventional image display method.

First, the retinal image can be generated without being subject to influences (diffraction, aberration, defocusing, etc.) of the optical properties of the eye 15 by employing a method in which the original image is formed on the retina 16 by focusing the coherent point light source pairs on the pupil plane A of the eye 15. Accordingly, the spatial resolution of the displayed image cannot be limited by the optical properties of the eye 15, and the original image can be generated in a high contrast even at high spatial frequencies. Therefore, even in case the observer's eye 15 is ametropic, it need not be corrected. In displaying the image on both eyes, moreover, visibility adjustment between the two eyes need not be carried out.

Secondly, the image display unit 11, unlike the case based on the known principle, is not conjugate with the retina 16, so that the spatial resolution of the displayed image cannot be limited by that of the display unit 11.

Thirdly, the field angle obtained with the present principle depends on the F-number of the eyepiece 14 or the size of the pixels of the image display unit 11 independently of the image resolution. Accordingly, a wide-field-angle, high-definition image can be formed on the retina by using a low F-number lens as the eyepiece 14 or by reducing the size of individual point light source images formed on the pupil plane A of the eye 15.

However, this principle involves a drawback that the retinal image is distorted depending on the observer's eye movements.

Figure 2A:
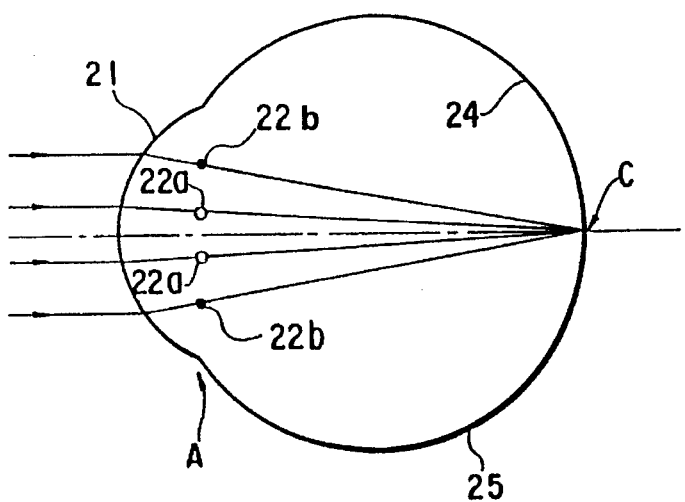
FIGS. 2A and 2B show the way a retinal image is distorted when an observer's eye moves.
Figure 2B:
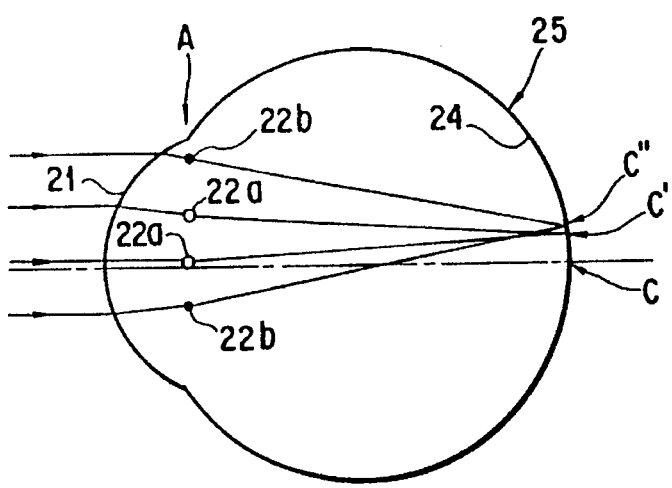

Referring now to FIGS. 2A and 2B, this drawback will be described.

The point light source pairs (only two spatial frequency components of which will be described for simplicity), generated and displayed by the image display unit (not shown), are refracted by the cornea 21 of an eye 25, and are then focused in the vicinity of the pupil plane A. As a result, two point light source pairs 22a and 22b are formed on the pupil plane A, as indicated by unfilled circles and filled circles in FIGS. 2A and 2B.

When the optical axis of the eye 25 is aligned with that of the image display unit, as shown in FIG. 2A, the point light source pairs 22a and 22b are arranged symmetrically with respect to the optical axis.

If the point light source pairs 22a and 22b share the same phase information, in this case, one of bright stripes of the interference fringes on the retina 24 is formed on an optical axis which is equally distant from the source pairs 22a and 22b. In FIG. 2A, symbol C represents a retinal position in which the aforesaid bright stripe is generated.

FIG. 2B shows a state obtained when the eye 25 is shifted downward in the plane of the drawing.

In this case, light beams incident upon the peripheral portion of the curved cornea 21 are refracted more than ones incident upon the central portion, so that the point light source pairs 22a and 22b focused on the pupil plane A are arranged asymmetrically with respect to the optical axis of the eye.

If the point light source pairs 22a and 22b share the same phase information, as in the case of FIG. 2A, retinal positions which are equally distant from the source pairs 22a and 22b vary depending on the spatial frequency, as indicated by symbols C' and C" in FIG. 2B.

The retinal positions C' and C" tend to move away from the retinal position C as the spatial frequency increases.

To generate a color image, point light source pairs with different wavelengths are formed on the pupil plane A and the refractive indices of optical media of the eye 25, such as the cornea 21, vary depending on the wavelength. Even though interference fringes with the same spatial frequency are formed on the retina 24, the movements of the observer's eye 25 cause the relative phase shift which degrades a retinal image.

In the image display optical system using the interference method, as described above, the relative phases of the interference fringes formed on the retina 24 are changed by the movements of the eye 25. Thus, this system has a disadvantage that the image is distorted by change of the direction of the observer's visual axis.

In order to eliminate this drawback, an image display apparatus based on the present invention is provided with a visual axis detecting unit for detecting the observer's visual axis and an image display correcting unit for restraining the distortion of the retinal image caused by the eye movements, within its tolerance range.

Conventionally, there have been proposed various methods for detecting the direction of the visual axis. Electrooculography (EOG) is a method in which the visual axis direction is detected by utilizing the characteristic that the cornea of the eye has a positive potential compared to the fundus. More specifically, it is a method for detecting the eye movements in accordance with potential differences obtained from a plurality of electrodes pasted on the observer's face.

FIG. 3A shows an optical system proposed as an alternative method. In this system, two infrared spots 35 emitted individually from two light sources 36 are projected to the boundary between the iris 32 and sclera 34 of an eye 31. Reflected light beams from the boundary are received by means of two light sensing elements 37. The elements 37 deliver electrical signals corresponding to received light intensity to a differential circuit 38. The circuit 38 executes a difference computation for these electrical signals, and outputs the result of the computation. The visual axis direction is detected in accordance with this computation result.

More specifically, the eye movements are determined by detecting the difference in intensity between the two reflected light beams from the boundary which is attributable to the movements of the eye 31.

FIG. 4 shows another practicable method, in which the visual axis direction and the movements of an eye 41 are determined by analyzing the positional relationships between reflected light beams (Purkinje images) from various optical interfaces (anterior surface of cornea 42, posterior surface of cornea 43, anterior surface of lens 44, posterior surface of lens 45, etc.) in the eye 41.

In another applicable method, the visual axis direction is determined by fetching a pattern of blood vessels on the fundus or an image processing of the pupil.

The following is a description of various embodiments of the present invention to which these principles are applied. In the description to follow, a "visual axis detector" represents a measuring device or means which employs any of the aforementioned visual axis detecting methods or an alternative method.

Referring first to FIG. 5, an image display apparatus according to a first embodiment of the present invention will be described. In the description of the present embodiment, like reference numerals or symbols are used to designate the same components of the image display optical system shown in FIG. 1, and a description of those components is omitted.

As shown in FIG. 5, the image display apparatus of the present embodiment comprises an image display unit 11, light transmission unit 17, visual axis detector 51, and image display correcting unit 52. The display unit 11 can generate and display a plurality of coherent point light source pairs (not an image itself intended to be displayed to the observer). The transmission unit 17 focuses the point light source pairs, generated and displayed by the display unit 11, on the pupil plane A of the observer's eye 15 so that an image is formed on the retina 16 of the eye 15 by the effect of optical interference. The detector 51 monitors the movements (e.g., in the direction of arrow T in FIG. 5) of the eye 15, thereby detecting the direction of the visual axis. The correcting unit 52 restricts a distortion of a retinal image, caused by the eye movements, within its tolerance range in accordance with the change of the visual axis direction detected by means of the visual axis detector 51.

The image display correcting unit 52 includes an optical member 53 rotatably mounted in an optical path between the image display unit 11 and a lens 12, and optical member drive means 54 for tilting the optical member 53 for a given angle in a predetermined direction (indicated by arrow S in FIG. 5).

The optical member 53, which is formed of a glass plate, for example, serves to shift images of the point light source pairs, generated and displayed by the image display unit 11, parallel to the optical axis as it is tilted in the direction of arrow S.

More specifically, when the optical member 53 is set at a position indicated by broken line in FIG. 5, the images of the point light source pairs generated and displayed by the image display unit 11 are guided to the light transmission unit 17, along an optical path indicated by broken line in FIG. 5, and are focused on the pupil plane A of the eye 15 by means of an eyepiece 14. Symbol $I_2$ designates the resulting focus position.

Subsequently, when the optical member 53 is tilted as indicated by the solid line in FIG. 5, the images of the point light source pairs are guided to the light transmission unit 17, along an optical path indicated by the solid line in FIG. 5 and shifting parallel to the optical path as indicated by the broken line, and are focused on the pupil plane A of the eye 15 by means of an eyepiece 14. Symbol $I_1$ designates the resulting focus position for this case.

As seen from FIG. 5, the point light source images generated and displayed by the image display unit 11 are shifted in parallel within the pupil plane A by tilting the optical member 53 for the given angle in the predetermined direction.

If the refractive index, thickness, and tilt angle of the optical member 53 are n, d and θ, respectively, a parallel shift X of the point light source images in the pupil plane A is given by $$X = \frac{f_2}{f_1} d \sin\theta \left\{ 1 - \frac{\cos\theta}{\sqrt{n^2 - \sin^2\theta}} \right\} \quad (1)$$

where $f_1$ and $f_2$ represent the focal lengths of the lens 12 and the eyepiece 14, respectively.

The direction and angle of the tilt of the optical member 53 are computed in accordance with visual axis direction data delivered from the visual axis detector 51.

Based on this visual axis direction data, the optical member drive means 54 controls the tilt of the optical member 53 so that the point light source images generated and displayed by the image display unit 11 can always be focused in place on the pupil plane A of the eye 15.

When the visual axis detector 51 detects an upward shift of the observer's eye 15 as shown by the arrow T in FIG. 5, for example, the visual axis detector 51 outputs the visual axis direction data to the optical member drive means 54. The optical member drive means 54 computes the direction and angle of the tilt of the optical member 53 in accordance with equation (1). Based on this computation result, the drive means 54 tilts the optical member 53 for the computed angle in the clockwise direction in the case as shown in FIG. 5. As a result, the point light source images generated and displayed by the image display unit 11 shift parallel so as to follow the direction and translation of the movements of the eye 15, whereupon they are focused on the same region of the pupil plane A.

Thus, according to the present embodiment, the point light source images can be focused on the same region of the pupil plane A so as to follow up the movement of the observer's eye 15 by controlling the direction and angle of the tilt of the optical member 53, so that the distortion of the retinal image caused by the movement of the observer's eye 15 can be restrained. Accordingly, a wide-field-angle, high-definition image can always be projected and displayed on the retina 16, corresponding to the direction of the observer's visual axis.

The present invention is not limited to the arrangement of the embodiment described above. For example, the optical member 53 may be located in an optical path between the eyepiece 14 and the eye 15 to obtain the same result. Moreover, in order to shift the point light source images two-dimensionally, the optical member 53 may be tilted or rotated around two different rotational axes (not shown) which are perpendicular to the optical axis by means of a motor or galvanometer.

Referring now to FIG. 6, an image display apparatus according to a second embodiment of the present invention will be described. In the description of the present embodiment, like reference numerals or symbols are used to designate the same components of the apparatus according to the first embodiment, and a description of those components is omitted.

The image display apparatus of the present embodiment is arranged so that the point light source images can be focused on the same region of the pupil plane A of the eye 15 by shifting the image display unit 11 itself for a given distance in the direction shown by the arrow X in FIG. 6.

To attain this, the image display apparatus of the present embodiment comprises the image display unit 11, movable in the direction shown by the arrow X in FIG. 6, and display position control unit 61 for moving the display unit 11 for the given distance in the predetermined direction.

The display position control unit 61 includes means for moving the image display unit 11 in the direction of arrow X in FIG. 6, e.g., a biaxial stage (not shown) such as an XY-stage, and is designed so that the biaxial stage can travel a given distance in a predetermined direction in accordance with the visual axis direction data delivered from the visual axis detector 51.

Now suppose that the observer's eye 15 has been moved upward in the direction shown by the arrow T in FIG. 6, from a position indicated by the broken line to a position indicated by the solid line, for example.

In this case, the visual axis detector 51 detects the direction and translation of the movements, and delivers the visual axis direction data to the display position control unit 61. Based on the visual axis direction data, the control unit 61 computes the direction and translation of the movement of the biaxial stage so that the point light source images generated and displayed by the image display unit 11 can be focused on the same region of the pupil plane A. Based on the result of this computation, moreover, the image position control unit 61 controls the movements of the biaxial stage, thereby moving the image display unit 11 downward for the given distance in the direction shown by the arrow X in FIG. 6. As a result, the point light source images are focused on the same region of the pupil plane A of the eye 15.

Thus, according to the present embodiment, the point light source images can be focused on the same region of the pupil plane A so as to follow up the movement of the observer's eye 15 by controlling the direction and translation of the movements of the image display unit 11, so that the distortion of the retinal image caused by the movements of the observer's eye 15 can be restrained. Accordingly, a wide-field-angle, high-definition image can always be projected and displayed on the retina 16, regardless of the direction of the observer's visual axis.

In a coherent optical system, a problem is aroused by the influence of interference noises which are produced by the reflection between optical components. According to the present embodiment, however, additional optical component is not required to the light transmission unit 17, so that the distortion of the retinal image caused by the movements of the eye 15 can be restrained efficiently.

Figure 7:
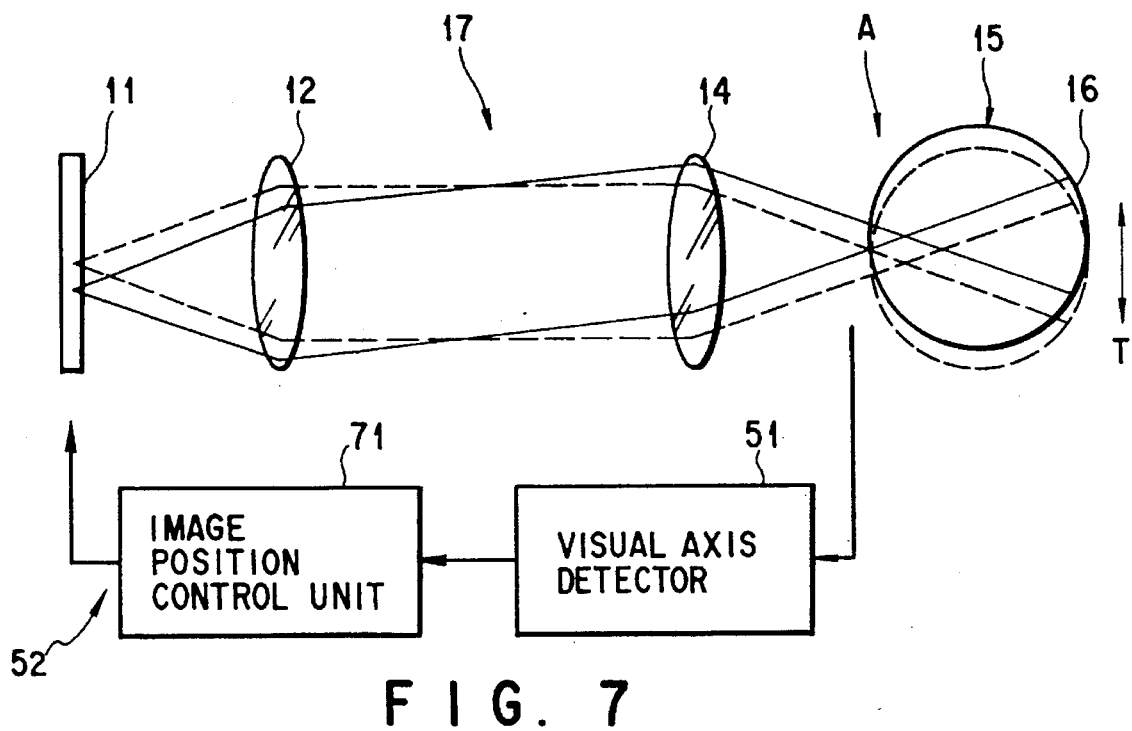
FIG. 7 is a schematic view showing an arrangement of an image display apparatus according to a third embodiment of the invention.

Referring now to FIG. 7, an image display apparatus according to a third embodiment of the present invention will be described. In the description of the present embodiment, like reference numerals or symbols are used to designate the same components of the apparatuses according to the foregoing embodiments, and a description of those components is omitted.

The image display apparatus of the present embodiment comprises an image position control unit 71 which serves to shift the point light source pairs, generated and displayed by the display unit 11, (instead of translating the image display unit 11 itself) for a given distance in a predetermined direction in accordance with the change of the direction of the observer's visual axis. For other arrangements, the apparatus of the present embodiment resembles the one shown in FIG. 6.

The movements of the point light source pairs themselves are controlled in accordance with the visual axis direction data delivered from the visual axis detector 51, and the image position control unit 71 controls the operation of the image display unit 11 in accordance with the visual axis direction data. Thus, the point light source pairs generated and displayed by the display unit 11 are formed for the given distance in the predetermined direction so that the point light source images can always be focused on the same region of the pupil plane A.

Now let's suppose that the observer's eye 15 has been shifted upward in the direction shown by the arrow T in FIG. 7, from a position indicated by broken line to a position indicated by solid line, for example.

In this case, the visual axis detector 51 detects the direction and coverage of the movements, and delivers the visual axis direction data to the image position control unit 71. Based on the visual axis direction data, the control unit 71 computes the direction and translation of the movements of the point light source pairs generated and displayed by the image display unit 11. Based on the result of this computation, moreover, the image position control unit 71 shifts the point light source pairs, generated and displayed by the display unit 11, downward for a given distance. As a result, the point light source images are focused on the same region of the pupil plane A of the eye 15.

Thus, according to the present embodiment, the point light source images can be focused on the same region of the pupil plane A so as to follow up the movements of the observer's eye 15 by controlling the direction and translation of the movements of the point light source pairs generated and displayed by the image display unit 11, so that the distortion of the retinal image caused by the movements of the observer's eye 15 can be restrained. Accordingly, a wide-field-angle, high-definition image can always be projected and displayed on the retina 16, corresponding to the direction of the observer's visual axis.

According to the present embodiment, the distortion of the retinal image attributable to the change of the visual axis direction can be restrained by means of software, without requiring the use of any driving unit. Therefore, the apparatus can be simplified in construction and reduced in size and weight.

Figure 8:
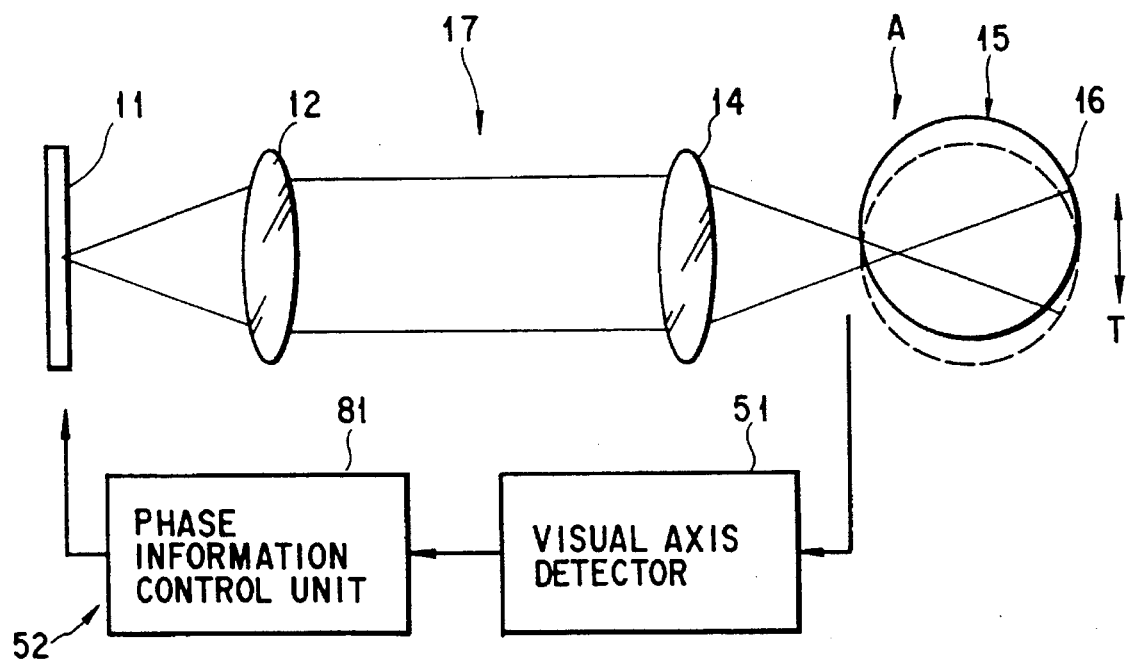
FIG. 8 is a schematic view showing an arrangement of an image display apparatus according to a fourth embodiment of the invention.

Referring now to FIG. 8, an image display apparatus according to a fourth embodiment of the present invention will be described. In the description of the present embodiment, like reference numerals or symbols are used to designate the same components of the apparatuses according to the foregoing embodiments, and a description of those components is omitted.

The image display apparatus of the present embodiment comprises an image display correcting unit or phase information control unit 81 which serves to control phase components of the Fourier-transform image generated and displayed by the image display unit 11, in accordance with the change of the direction of the observer's visual axis. For other arrangements, the apparatus of the present embodiment resembles the one shown in FIG. 7.

Control of the phase components after Fourier transform is carried out on the basis of the visual axis direction data delivered from the visual axis detector 51.

More specifically, the phase information control unit 81 first computes phase error components generated individually in the spatial frequency components, on the basis of the visual axis direction data. Then, the control unit 81 subtracts these phase error components from the phase components of the Fourier-transformed image generated and displayed last by the image display unit 11. Thereafter, the unit 81 sets the resulting computation values as phase components of a Fourier-transformed image to be generated and displayed next by the display unit 11.

The Fourier-transformed image can always be focused on the same region of the pupil plane A of the observer's eye 15 by setting the phase components so as to cancel all the phase error components generated by the movement of the eye 15. As a result, a wide-field-angle, high-definition image can be projected and displayed on the retina 16 without causing a distortion of the retinal image attributable to the movements of the observer's eye 15.

As described with reference to FIG. 2, an image can be presented at any retinal location without distorting the retinal image by setting the phase components so as to cancel only the phase error components attributed to variations in the position and angle of incidence of light beams on the cornea (caused by the movements of the eye 15).

Thus, according to the present embodiment, the point light source images can be focused on the same region of the pupil plane A so as to follow up the movements of the observer's eye 15 by controlling the phase components of the Fourier-transformed image, so that the distortion of the retinal image caused by the movements of the observer's eye 15 can be restrained. Moreover, it allows us to present the image at the observer's desired retinal region in accordance with the change of the visual axis direction. Accordingly, a wide-field-angle, high-definition image can be always projected and displayed on the retina 16, corresponding to the direction of the observer's visual axis.

According to the present embodiment, the distortion of the retinal image attributable to the change of the visual axis direction can be restrained by means of software, without requiring the use of any driving unit. Therefore, the apparatus can be simplified and reduced its size and weight.

The following is a description of an image display apparatus according to a fifth embodiment of the present invention.

The present invention is based on a combination of the fourth embodiment and one of the first to third embodiments, and is designed so as to present different image regions corresponding to the change of the visual axis direction while continually focusing the Fourier-transformed image, generated and displayed by the image display unit 11, in the vicinity of the center of the pupil (not shown).

Meanwhile, the fourth embodiment is designed so that the Fourier-transformed image can always be focused on the same region of the pupil plane A of the observer's eye 15 by setting the phase components so as to cancel all the phase error components generated by the movements of the eye 15.

If the movements of the eye 15 is substantially large, however, the Fourier-transformed image generated and displayed by the image display unit 11 is focused on the peripheral portion of the pupil plane A of the eye 15.

In general, the efficiency of light captured by the retina 16 depends on the portion of the pupil through which the light passes (Stiles-Crawford effect).

The peak of this efficiency (Stiles-Crawford maximum) is slightly deviated from the center of the pupil, and the efficiency lowers substantially symmetrically with distance in all directions from the Stiles-Crawford maximum.

If the Fourier-transformed image generated and displayed by the image display unit 11 is focused on the peripheral portion of the pupil plane A, therefore, the effective intensity of each point light source may be so low that the retinal image is dark, or the contrast of the retinal image may be lowered by unevenness of the effective intensity of each point light source of the pair.

In order to eliminate this drawback and to attain the aforesaid object, therefore, the present embodiment is arranged as follows.

First, the movements of the observer's eye 15 is detected by means of the visual axis detector 51 on the basis of the arrangements of the first to third embodiments (see FIGS. 5 to 7), and the Fourier-transformed image generated and displayed by the image display unit 11 is always focused on the same region of the pupil plane A of the eye 15 in accordance with the visual axis direction data.

In the image display unit 11, in this case, values obtained by subtracting phase components corresponding to the movements of the Fourier-transformed image (i.e. components simply proportional to the spatial frequency) from the phase components of the Fourier-transformed image generated and displayed last by the display unit 11 are set as new phase components.

This produces the same effect as the one obtained when the new phase components are set so as to cancel only those phase errors which are attributable to the eye movements or the variations in the position and angle of incidence of the light beams on the cornea. As in the case of the fourth embodiment (see FIG. 8), therefore, various regions of the displayed image can be observed corresponding to the change of the visual axis direction.

Thus, by combining the arrangements of the first to third embodiments with the arrangement in which the phase components of the Fourier-transformed image are controlled, the distortion of the retinal image attributable to the movement of the observer's eye 15 can be restrained, and an image corresponding to the direction of the observer's visual axis can always be presented with high luminance and high contrast.

In correcting the retinal image by processing phase information for the Fourier-transformed image (refer to fourth and fifth embodiments) and generating a color image by processing different wavelength components, moreover, phase components must be computed and set individually for the various wavelength components which constitute the image, in consideration of differences between the respective refractive indices of the optical media of the eye 15.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An image display apparatus comprising:

display means for generating and displaying a plurality of coherent point light source pairs;

optical means for focusing images of the point light source pairs, generated and displayed by the display means, on the pupil plane of an eye of an observer so that an image is formed on the retina by the effect of optical interference;

visual axis detecting means for detecting a visual axis direction of the observer's eye; and an optical correcting unit for reducing a distortion of the retinal image, caused by eye movement, in accordance with the visual axis direction detected by the visual axis detecting means.

2. An image display apparatus according to claim 1, wherein said optical means includes lens means for establishing an optically conjugate positional relation between the display means and the pupil plane of the eye of the observer so that the images of the point light source pairs displayed by the display means are formed on the pupil plane of the observer's eye.

3. An image display apparatus according to claim 2, wherein said lens means includes first and second lenses, the display means being situated on the primary focal plane of the first lens, the pupil plane of the eye of the observer being situated on the secondary focal plane of the second lens, and the secondary focal plane of the first lens being coincident with the primary focal plane of the second lens.

4. An image display apparatus according to claim 1, wherein said visual axis detecting means includes a light source unit for applying a light flux to the eye of the observer by irradiation, a detecting unit for receiving a reflected light beam from the eye and detecting an optical change of the reflected light beam caused by eye movement, and a computing unit for computing the visual axis direction of the eye in accordance with the optical change detected by the detecting unit.

5. An image display apparatus according to claim 4, wherein said light source unit includes first and second light sources for applying two infrared rays to the boundary between the iris and sclera of the eye by irradiation, said detecting unit includes first and second light sensing elements for receiving two reflected light beams from the boundary and outputting electrical signals corresponding to the quantities of light received, and said computing unit includes a differential circuit for obtaining a difference in magnitude between the electrical signals output by the first and second light sensing elements.

6. An image display apparatus according to claim 1, wherein said optical correcting unit includes an optical member rotatably mounted so that the images of the point light source pairs generated and displayed by the display means are focused on the same region of the pupil plane of the eye, and optical member drive means for tilting the optical member for a given angle in a predetermined direction in accordance with the visual axis direction of the eye detected by the visual axis detecting means.

7. An image display apparatus according to claim 1, wherein said optical correcting unit includes a display position control unit for moving the display means for a given distance in a predetermined direction, in accordance with the visual axis direction of the eye detected by the visual axis detecting means, so that the images of the point light source pairs generated and displayed by the display means are focused on the same region of the pupil plane of the eye.

8. An image display apparatus according to claim 1, wherein said optical correcting unit includes an image position control unit for controlling a generating/displaying position for the point light source pairs generated and displayed by the display means, in accordance with the visual axis direction of the eye detected by the visual axis detecting means, so that the images of the point light source pairs generated and displayed by the display means are focused on the same region of the pupil plane of the eye.

9. An image display apparatus according to claim 1, wherein said optical correcting unit includes a phase information control unit for removing phase error components produced by the observer's eye movement from phase components of the images of the point light source pairs generated and displayed by the display means, in accordance with the visual axis direction of the eye detected by the visual axis detecting means, so that the images of the point light source pairs generated and displayed by the display means are always focused on the same region of the pupil plane of the eye.

10. An image display apparatus according to claim 6, wherein said optical correcting unit includes a phase information control unit for removing phase error components produced by the observer's eye movement from phase components of the images of the point light source pairs generated and displayed by the display means, in accordance with the visual axis direction of the eye detected by the visual axis detecting means, so that the images of the point light source pairs generated and displayed by the display means are always focused on the same region of the pupil plane of the eye.

11. An image display apparatus according to claim 7, wherein said optical correcting unit includes a phase information control unit for removing phase error components produced by the observer's eye movement from phase components of the images of the point light source pairs generated and displayed by the display means, in accordance with the visual axis direction of the eye detected by the visual axis detecting means, so that the images of the point light source pairs generated and displayed by the display means are always focused on the same region of the pupil plane of the eye.

12. An image display apparatus according to claim 8, wherein said optical correcting unit includes a phase information control unit for removing phase error components produced by the observer's eye movement from phase components of the images of the point light source pairs generated and displayed by the display means, in accordance with the visual axis direction of the eye detected by the visual axis detecting means, so that the images of the point light source pairs generated and displayed by the display means are always focused on the same region of the pupil plane of the eye.

* * * * *